United States Patent [19]

Holaday et al.

[11] 4,434,168

[45] Feb. 28, 1984

[54] NARCOTIC ANTAGONISTS IN THE THERAPY OF SHOCK

[75] Inventors: John W. Holaday, Rockville, Md.; Alan I. Faden, Washington, D.C.

[73] Assignee: The United States of America as represented by the Secretary of the Army, Washington, D.C.

[21] Appl. No.: 248,622

[22] Filed: Mar. 27, 1981

Related U.S. Application Data

[63] Continuation-in-part of Ser. No. 3,699, Jan. 16, 1979, Pat. No. 4,267,182.

[51] Int. Cl.³ ............................................. A01N 43/42
[52] U.S. Cl. ...................................... 424/260; 424/95
[58] Field of Search ............... 424/260; 260/112.5 TR

[56] References Cited

PUBLICATIONS

Tony L. Yaksh et al., European Journal of Pharmacology, vol. 46, 1977, pp. 83–92.
L. D. Byrd, Psychopharmacology, vol. 49, 1976, pp. 225–234.
J. David Leander, Psychopharmacology, vol. 50, 1976, pp. 211–213.
Clifford J. Woolf et al., European Journal of Pharmacology, vol. 45, 1977, pp. 311–314.
Chemical Abstracts, 1978, vol. 88, p. 69112x, Yaksh et al.
Chemical Abstracts, 1976, vol. 85, p. 171810y, Byrd.
Chemical Abstracts, 1978, vol. 88, p. 32035y, Woolf et al.
Chemical Abstracts, 1977, vol. 86, p. 12304v, David.

*Primary Examiner*—Dale R. Ore
*Attorney, Agent, or Firm*—William G. Gapcynski; Werten F. W. Bellamy; John M. Petruncio

[57] ABSTRACT

The use of narcotic antagonists (e.g., naloxone) in shock therapy is disclosed.

18 Claims, No Drawings

NARCOTIC ANTAGONISTS IN THE THERAPY OF SHOCK

The invention described herein may be manufactured, used, and licensed by or for the Government for governmental purposes without the payment to use of royalties thereon.

CROSS-REFERENCE TO RELATED APPLICATION

The present application is a continuation-in-part of a copending application Ser. No. 3,699, filed on Jan. 16, 1979, entitled "Narcotic Antagonists in the Therapy of Shock," and now U.S. Pat. No. 4,267,182, issued May 12, 1981.

FIELD OF THE INVENTION

The field of invention relates to the therapy of shock, which is defined in Blakiston's New Gould Medical Dictionary, 2d, ed., page 1092 (McGraw-Hill, N.Y., 1956) as follows: "The clinical manifestations of an inadequate volume of circulating blood accompanied by physiologic adjustments of the organism to a progressive discrepancy between the capacity of the arterial tree and the volume of blood to fill it." A primary characteristic of shock is hypotension. Current attempts at treatment involve the administration of isoosmotic fluids such as blood, plasma, or volume expanders (e.g., albumin) in conjunction with vasoactive agents such as dopamine. However, such attempts are often ineffective, because they are aimed at treating the effects of shock (inadequate perfusion) instead of its causes. There are serious drawbacks associated with such attempts: (1) time is required for blood typing and/or setting up intravenous systems for administering blood or other isoosmotic fluids; (2) blood pressure must be constantly monitored when vasoactive agents such as dopamine are administered; (3) current treatments can be administered only in a clinical environment, and potential life-threatening time delays usually occur between diagnosis and treatment; and (4) moreover, such attempts are not always successful in the management of shock syndromes.

DESCRIPTION OF THE PRIOR ART AND PRIOR ART STATEMENT

The following discussion will highlight the significant and material distinctions between the novel method involved in the instant invention and those described in prior publications. A careful review of the prior literature clearly reveals that the type of shock contemplated and being treated by applicants as compared to that involved in the prior publications is completely different. Each of the prior publications relate to "shock" induced by an electrical stimulus used to produce nociceptive (painful) responses in experimental animals in order to test the behavioral and/or analgesic effects of endogenous and exogenous opiate substances. On the other hand, applicants' invention is directed to the therapeutic treatment of shock experienced by an animal which results from inadequate circulating blood volume in the body's arterial system. The type of "shock" being treated by applicants' method is that resulting from low blood pressure whereas the prior publications relate to "shock" caused by a noxious electrical stimulus. Applicants' invention relates to the therapeutic treatment of "shock" resulting from either the loss of a substantial volume of blood from the body (massive bleeding) or other physiological conditions of the body which prevents the circulation of an adequate volume of blood throughout the arterial system. The non-pertinent nature of the cited references is further highlighted by the fact that blood pressure or cardiovascular function is neither mentioned nor suggested.

In fact, applicants' review of the full text of the prior publications mentioned below reveals the following summary of their respective teachings.

The article by Tony L. Yaksh et al, European Journal of Pharmacology, Volume 46 (1977), pages 83–92 describes a study in which monkeys receive electrical shocks across their feet as a painful stimulus. Drugs are administered which alter the animal's perception of the intensity of this pain as indicated by the animal's behavior in response to the electric foot shock. These studies merely indicate the pain relieving aspects of opiate drugs and bear no relationship to cardiovascular function.

Similarly, the article by L. D. Byrd, Psychopharmacology, Volume 49 (1976), pages 225–234 describes a study wherein painful electrical shocks are administered to monkeys to monitor the effects of pain relieving drugs in combination with other drugs which also modify animal behavior. Here again, no relationship to cardiovascular function or dysfunction is apparent.

In the article by J. David Leander, Psychopharmacology, Volume 50 (1976), pages 211–213 a study is described wherein electric shocks were administered to produce painful responses in pigeons, and the effects of naloxone in altering the painful aspects of these electrical shocks are studied. Again, this study has no bearing on blood pressure but relates to pain responses to electrical shock and the effects of drugs which alter pain.

Finally, the article by Clifford J. Woolf et al, European Journal of Pharmacology, Volume 45 (1977), pages 311–314 describes a study wherein low voltage electrical shock is administered to rats so as to produce changes in pain thresholds. It shows that low voltage electrical currents delivered to pain processing centers of the brain and spinal cord turn on the body's own opiate, or pain relieving systems. This relates to electrically-induced modification of pain intensity and has no relationship to blood pressure or cardiovascular function.

Applicants novel method is directed to the therapeutic use of narcotic antagonists to reverse or prevent the pathologic states resulting from an inadequate blood perfusion of vital organs (i.e., circulatory shock). The prior publications mentioned supra have no bearing whatsoever on the cardiovascular system. Instead, in those articles an electrical shock is used to evaluate pain responses. The endogenous opiate system is known to be involved in pain systems, however, the involvement of the endogenous opiate system in the pathological cardiovascular sequellae of circulatory shock is the novel finding of the applicants. Thus, at least two distinct physiological responses (i.e. pain and circulatory shock) involve a common endogenous opiate system. In the same manner that steroid drugs are used to treat a variety of distinctly different disease states (from leukemia to dermatitis), narcotic antagonists are used by the applicants to reverse circulatory shock, rather than to alter pain perception. In fact, narcotic antagonists are shown in the articles mentioned supra to worsen the perception of the pain produced by electric shocks. Obviously, there is no therapeutic value in drugs which intensify pain. These same drugs, however, improve function and survival in circulatory shock states.

Applicants' therapeutic use of narcotic antagonists in treating spinal injuries as compared to the use of narcotic antagonists as a tool to evaluate pain responses by Woolf et al (European Journal of Pharmacology, Volume 45, page 311, 1977) further reveal the distinctions between these scientic applications. Woolf et al are evaluating an analgesic effect of electric currents externally applied to the base of the tail of rats. Much like acupuncture-induced pain relief, small electric currents (also used in acupuncture) turn on the body's own pain relieving circuits. By measuring how long rats will leave their tail immersed in very hot water, an index of "pain responses" is obtained by Woolf et al. Since pain signals are known to be transmitted by spinal-cord nerve cells to the brain, they sought to determine if endogenous narcotics (endorphins) in the brain or in spinal cord nerves were involved in these analgesic states. To test this, they showed that if these pain signals are interrupted by cutting the spinal cord in the lower thoracic region, narcotic antagonists still reversed the externally delivered electric shock-induced analgesia. They concluded from these results that the body's own narcotic system (endorphins) mediates pain responses at a spinal reflex level that does not involve transmission to the brain. Thus, these authors are studying a situation analogous to placing a hand on a hot stove. Reflex action at the spinal cord level results in removal of the hand before the brain even knows of the painful burn. Their findings are neither directly nor impliedly related to blood pressure, heart function, or any form of circulatory shock. Furthermore, the following significant distinctions over the Woolf et al article should be noted:

1. Woolf et al are applying an external electrical stimulus (electric shock), whereas the circulatory collapse accompanying spinal trauma or transection (circulatory shock) does not involve electricity and is instead an internally generated pathological response to injury;
2. Woolf et al cut through the lower thoracic spinal cord to evaluate pain, whereas our studies evaluated the cardiovascular consequence of cervical spinal cord injury;
3. Woolf et al cut through the lower-spinal cord as a secondary tool to evaluate the pain circuits between the tail and the brain, whereas the applicant's primary purpose was to transect the upper (cervical) spinal cord to evaluate the circulatory shock state that results;
4. Woolf et al administer naloxone (a narcotic antagonist) first, then continuously apply small electric shocks to the base of the tail for 30 minutes before they evaluate the pain response to immersion of the tail in hot water. They repeat the same procedure in rats following lower thoracic spinal-cord interruption of pain signals. By contrast, the applicants initially cut through or injure the cervical spinal cord and then wait for blood pressure and other cardiovascular parameters to fall. After this circulatory shock state occurred (30–45 minutes after cervical-cord injury) naloxone is given to reverse the circulatory shock state and thus improve blood pressure and cardiac function;
5. The sole objective of Woolf et al is to evaluate pain systems using small electric shocks to produce analgesia. The applicants sole objective is to evaluate cardiovascular function and its consequences following spinal cord injury;
6. Woolf et al use unanesthetized rats in order to evaluate pain responses, whereas the applicants required use of anesthetized rats and cats to block pain responses while they evaluated the cardiovascular system; and
7. Woolf et al used a narcotic antagonist as a tool to evaluate pain systems, not to suggest a therapeutic use. The applicants have used narcotic antagonists to specifically evaluate their therapeutic utility in reversing the shock state which follows cervical spinal cord injury.

SUMMARY OF THE INVENTION

Accordingly, there is a need for an improved method of shock therapy. It is an object of this invention to provide such a method.

Another object of the invention is to treat shock at a causal level, instead of attempting to treat only the effects of shock.

Another object of the invention is to provide a treatment of shock which may be administered rapidly, thus eliminating the potentially life-threatening time delays now required.

Another object of the invention is to provide a method of treating shock without the need to monitor blood pressure continuously.

Another object of the invention is to treat shock with a known class of drugs.

Yet another object of the invention is to provide a pretreatment for animals with inadequate adrenal function, in order to protect them from their hypersensitivity to shock states, preceding surgery or other anticipated trauma.

Still other objects of this invention will become apparent to those of ordinary skill in the art upon reading this disclosure.

The above objects are achieved by the improved method of shock therapy of this invention, which embraces: (1) a method of treating an animal which is suffering from shock by administering to said animal a therapeutically effective amount of a drug selected from the group consisting of narcotic antagonists and the pharmaceutically-acceptable acid addition salts thereof; and (2) a method of pretreating an animal in order to protect it from shock by administering to said animal a therapeutically effective amount of a drug selected from the group consisting of narcotic antagonists and the pharmaceutically-acceptable acid addition salts thereof.

The term "animal" in this disclosure refers to any organism which is capable of suffering from shock.

It is believed that narcotic antagonists and their pharmaceutically-acceptable acid addition salts possess therapeutic value for treating all forms of shock, inclusive of but not restricted to the following forms of circulatory shock states:

anaphylactic,
anaphylactoid,
burn,
cardiogenic
hematogenic (hemorrhagic, wound, hypovolemic),
nervous,
neurogenic (fainting),
restraint,
septic (vasogenic, endotoxic),
spinal injury (spinal shock, spinal trauma),
traumatic.

Nervous shock and restraint shock can be grouped as subcomponents of neurogenic shock. The common denominator of these forms of shock is the pressured occurrence of vasodilation leading to low blood pressure and reduction in both venous return and in cardiac output. The etiology of these forms of shock is considered to be relatively independent of primarily invasive causes of shock such as bacterial infections or overt blood loss through hemorrhage; however, neurogenic shock may be an important secondary component following such invasive insults on normal body function. For example, the psychophysiological consequence of seeing a bleeding wound or feeling intense pain may result in syncope (i.e. fainting) even though the blood loss from the wound per se in inadequate to cause true hemorrhagic shock. Nonetheless, nervous shock may thus be considered to be a distinct form of shock which relates to pathophysiological responses following psychic trauma. Restraint shock, in a similar manner, appears not to involve an external invasion of the body by bacteria or foreign objects which might produce a wound, but instead it results from the psychic trauma of forced immobilization. Thus, nervous shock, restraint shock, and neurogenic shock all involve a similar acute decrease in cardiovascular function in response to psychic trauma which may or may not be secondary to an invasive occurrence. Since "neurogenic" specifically translates to "having its origin in nerves" and since psychic trauma appears to be fundamentally involved, it seems appropriate to categorize nervous and restraint shock as specific forms of the more general category of neurogenic shock, all of which are believed to respond to narcotic antagonist therapy.

Spinal shock and spinal trauma should be considered as separate components of a general form of shock that occurs following spinal injury. Spinal shock is defined as a temporary condition of flaccid paralysis and areflexia following rapid functional transection of the spinal cord rostral to the overflow to affected muscles. This also includes cardiovascular manifestations of decreased blood pressure accompanying decreased cardiac output and lowered ventricular contractility. Thus, normal function of the heart (which is also a muscle) is severely impaired by transection (i.e. cutting through) of the spinal cord, particularly in the cervical spinal areas which mediate brain control over the cardiovascular system. Spinal trauma produces the same kind of decreases in cardiovascular function as does spinal shock except that the spinal cord is not transected, but instead bruised by some non-penetrating force (such as would occur following a diving board accident or severe whiplash in an automobile). We have demonstrated that narcotic antagonists improve blood pressure, cardiac contractility, and spinal cord perfusion following both spinal shock (transection) and spinal trauma (blunt injury), collectively referred to as occurring following spinal injury. Moreover, when the spinal trauma was followed by narcotic antagonist treatment, significantly less paralysis was shown to occur since the resulting improvement in blood flow to the injured spinal cord prevented cell death.

The collective spinal trauma forms of shock are a direct consequence of an external invasive process which either transected the spinal cord or in some way injured the cord. Thus, spinal trauma produces a shock state which is distinct from neurogenic shock defined above (although the psychic injury of spinal trauma may result in a secondary neurogenic shock as an additional complication).

Traumatic shock cannot be grouped under any of the aforementioned forms of shock since it is a distinct hybrid of two or more shock states. The word "trauma" involves the application of an injury by physical or mechanical agents, thus it requires an external invasive process. However, since psychic injury is believed to be a strong component of traumatic shock, a neurogenic origin of the cardiovascular pathophysiology must also be considered. Traumatic shock results in a functional decrease in circulating blood due to internal bleeding, blood sequestration in muscles or organs, as well as decreased cardiac output and lowered contractility resulting from a neurogenic cause.

The three general forms of shock discussed above (neurogenic, spinal injury, and traumatic) are all related to the fundamental definition of "shock" as a decrease in the perfusion of vital organs by blood which can progressively lead to cell death and, unless reversed, loss of normal function and even death of the organism. The cardiovascular pathophysiology which underlies these forms of shock appears to involve endogenous opiate (endorphin) systems since narcotic (opiate) antagonist treatment improves the shock state as indicated by direct measurements of blood pressure, cardiac contractility, tissue perfusion, and organism function.

Moreover, the classification of a drug as a pure narcotic antagonist or partial antagonist warrants its inclusion in this invention for use in shock therapy. Pure antagonists such as naloxone are included, as well as other drugs which possess varying degrees of morphine-like or agonist activity together with their antagonist activity. The invention includes, but is not restricted to, the following narcotic antagonists:

naloxone,
naltrexone,
nalorphine,
diprenorphine,
lavallorphan,
pentazocine,
metazocine,
cyclazocine,
etazocine,
peptide drugs with opiate receptor antagonistic activity.

Also, any drug with demonstrable agonist activity can be imparted with antagonist activity by the addition of an aliphatic group to its nitrogen moiety (e.g., nalorphine is N-allylnormorphine), and the use of such drugs is included within the scope of this invention.

The use of pharmaceutically-acceptable acid addition salts of narcotic antagonists is also within the scope of the invention. In general, any suitable inorganic or organic acid may be used to prepare such salts. Non-limiting examples of suitable inorganic acids are hydrochloric, hydrobromic, sulfuric, nitric, phosphoric, phosphorous, and perchloric acids. Non-limiting examples of suitable organic acids are tartaric, citric, acetic, succinic, maleic, malic, fumaric, oxalic, ascorbic, benzoic, lactic, palmitic, pamoic, lauric, stearic, oleic, myristic, lauryl sulfuric, linoleic, and linolenic acids.

Whether treating an animal for shock or pretreating it in order to protect it from shock, any suitable route of administration may be used depending on the particular drug administered. For example, one of ordinary skill can select from the intravenous, intramuscular, subcutaneous, parenteral, oral, and intrathecal routes of administration. The dose of drug contemplated is, broadly, a therapeutically effective amount; a preferred range is about 0.01 mg per kg to about 10 mg per kg body weight of animal.

EXPERIMENTAL DETAILS

The following description provides the salient features of laboratory tests which lead to the conclusion that narcotic antagonists and their pharmaceutically-acceptable acid addition salts are useful in the therapy of shock. However, applicants do not wish to be limited by the particular experimental details which were used in conducting these tests.

Initially, the endotoxin model of septic shock was chosen for testing. Male Wistar rats (Walter Reed strain) weighing 275–300 g were prepared with two indwelling cannulae, one in the tail artery for blood pressure monitoring and the other in the external jugular vein for drug administration. From 1–2 days after surgery, these conscious and alert rats were injected intravenously with 4 mg *Escherichia coli* lipopolysaccharide endotoxin. This injection of endotoxin usually produced a rapid fall in blood pressure, from an average mean arterial pressure (MAP) of 95 mm Hg to an MAP of 65–70 mm Hg, within 15 min. When MAP dropped to this low value, naloxone hydrochloride was injected intravenously at a dosage of 10 mg per kg in one half of the rats; the other half received placebo (saline) injections. The rats which received naloxone experienced a return of blood pressure to within normal ranges within 5 seconds, whereas placebo-injected rats experienced no increase in blood pressure. This striking difference between naloxone-treated and saline-control rats was confirmed in separate studies using 9–10 rats per group. Naloxone in the absence of endotoxin, however, was without effect on MAP. For further experimental details and results, the reader is referred to J. W. Holaday et al, Nature 275: 450–51 (5 October 1978).

Studies in the rat-endotoxin shock model were expanded to assess the effect of different doses of naloxone on MAP. In these tests, the rats were injected intravenously with 40 mg per kg *Escherichia coli* lipopolysaccharide endotoxin. Three doses of naloxone hydrochloride (0.1 mg per kg; 1.0 mg per kg; and 10.0 mg per kg) were chosen, and all doses successfully reversed endotoxin-induced hypotension in contrast to saline. Survival at 24 hrs was also monitored. Naloxone had no apparent effect on rat survival, although naloxone-injected rats were normotensive or hypertensive at death while saline-control rats were significantly hypotensive. This suggests that factors other than blood pressure maintenance are determinants of survival after endotoxin administration in the rat. However, the more precipitous the fall in blood pressure following endotoxin, the more rapid and complete its reversal by naloxone injections.

In addition to the endotoxin model of septic shock in rats, the efficacy of naloxone hydrochloride in reversing the hypotension produced by hypovolemic shock was tested. Conscious rats were partially exsanguinated through the intravenous cannulae while blood pressure was again monitored through the tail artery cannula. Approximately one half of the estimated total blood volume was removed. In a 250–300 g rat, this amounted to 9–10 ml blood, removed as needed to maintain an MAP of 35–40 mg Hg over 20 min. Either naloxone hydrochloride (1.0 mg per kg) or saline was then administered intravenously, and blood pressure was monitored for an additional 2 hrs. Survival over 24 hrs was also determined. Based on results in 30 rats, naloxone significantly improved blood pressure in this model of hypovolemic shock. Furthermore, 24 hr survival was also affected, since 7/15 saline-control rats died and only 2/15 of the naloxone-treated rats died.

Tests on the efficacy of naloxone in reversing the hypotension produced by rapid severing of the cervical spinal cord in the cat and rat have also been performed. In these studies, naloxone restored MAP toward normal values in doses between 0.1 mg per kg and 10 mg per kg in two cats and 30 rats. Therefore, in this model of spinal shock, once again naloxone improved MAP significantly.

Finally, studies have been conducted with dogs in both the endotoxic and hypovolemic shock models. In both models, naloxone-treated dogs showed improvement in all essential cardiovascular indices, including mean arterial pressure, systolic arterial blood pressure, diastolic arterial blood pressure, cardiac output, cardiac contractility, and heart rate. Moreover, survival was significantly improved in both models by naloxone treatment.

DISCUSSION

The successful test results in connection with various shock forms provide ample evidence that the specific opiate antagonist naloxone is efficacious for the treatment of shock, regardless how induced. Without being bound by any theory, it seems likely that endogenous opiates (endorphins) are released during shock states and that they contribute to hypotension, which is a primary characteristic of shock. See J. W. Holaday et al supra. The antagonist naloxone significantly reverse this hypotension. Accordingly, there is rational basis to believe that narcotic antagonist in general have direct therapeutic value in treating the various forms of shock. Narcotic antagonists appear to treat shock-hypotension at a causal level, because they block the hypotensive effects of the body's own substances which contribute to this pathophysiological state.

Among the narcotic antagonists, naloxone is a preferred drug for use in shock therapy because it increases blood pressure toward normal values within seconds after administration. Since naloxone is without effect on blood pressure in normal animals, the risk of over-correcting and causing hypertension or related effects by overdosage is minimal. Moreover, naloxone is currently available as a treatment for narcotic overdosages in humans.

The novel method of this invention may use narcotic antagonists to reverse ischemic damage following central nervous system insult. This not only includes spinal-cord trauma, but evidence indicates its more generalized efficacy in the treatment of the neurologic sequellae following head injury. Thus, such drugs as naloxone and other opiate antagonists are expected to have therapeutic efficacy in treating neurogenic shock (including nervous and restraint shock), spinal injury (including spinal shock and spinal trauma) and head injury.

The prevention of neurological damage following spinal cord trauma was recently demonstrated by the applicants. Following exposure of the cervical spinal cord, a 500 gram/centimeter force was applied to the surface of the dura in anesthetized cats. This results in a disabling quadraparesis in untreated animals. However, injections of naloxone 45 minutes following spinal cord injury was shown to significantly diminish paralysis when neurologic signs were evaluated 1 day as well as 1, 2, and 3 weeks following injury. The median naloxone-treated cat was ultimately able to stand and walk, whereas inert saline-treated animals were significantly more paralyzed.

We claim:

1. A method of treating an animal which is suffering from a form of shock selected from the group consisting of neurogenic, spinal and traumatic which comprises administering to said animal a therapeutically effective amount of a narcotic antagonist drug selected from the group consisting of naloxone, naltrexone, nalorphine, diprenorphine, levallorphan, pentazocine, metazocine, cyclazocine, etazocine, and the pharmaceutically-acceptable acid addition salts thereof.

2. The method of claim 1 wherein the animal is suffering from neurogenic shock.

3. The method of claim 2 wherein the drug is naloxone hydrochloride.

4. The method of claim 1 wherein the animal is suffering from spinal shock.

5. The method of claim 4 wherein the drug is naloxone hydrochloride.

6. The method of claim 1 wherein the animal is suffering from traumatic shock.

7. The method of claim 6 wherein the drug is naloxone hydrochloride.

8. The method of claim 1 wherein the drug is selected from the group consisting of naloxone and the pharmaceutically-acceptable acid addition salts thereof.

9. The method of claim 8 wherein the drug is naloxone hydrochloride.

10. A method of pretreating an animal in need thereof from a form of shock selected from the group consisting of neurogenic, spinal and traumatic which comprises administering to said animal a therapeutically effective shock preventing amount of a narcotic antagonist drug selected from the group consisting of naloxone, naltrexone, nalorphine, diprenorphine, levallorphan, pentazocine, metazocine, cyclazocine, etazocine and the pharmaceutically-acceptable acid addition salts thereof.

11. The method of claim 10 wherein the animal is suffering from neurogenic shock.

12. The method of claim 11 wherein the drug is naloxone hydrochloride.

13. The method of claim 10 wherein the animal is suffering from spinal shock.

14. The method of claim 13 wherein the drug is naloxone hydrochloride.

15. The method of claim 10 wherein the animal is suffering from traumatic shock.

16. The method of claim 15 wherein the drug is naloxone hydrochloride.

17. The method of claim 10 wherein the drug is selected from the group consisting of naloxone and the pharmaceutically-acceptable acid addition salts thereof.

18. The method of claim 17 wherein the drug is naloxone hydrochloride.